United States Patent [19]

Lorier et al.

[11] Patent Number: 5,013,568
[45] Date of Patent: May 7, 1991

[54] METHOD FOR TREATING FISH WITH ALPHA-2-MACROGLOBULIN

[75] Inventors: Michel A. Lorier; Brian L. Aitken, both of Christchurch, New Zealand

[73] Assignee: Life Technologies, Inc., Gaithersburg, Md.

[21] Appl. No.: 530,592

[22] Filed: May 30, 1990

[30] Foreign Application Priority Data

Jun. 1, 1989 [NZ] New Zealand .................. 229385

[51] Int. Cl.$^5$ .............................................. A23L 1/325
[52] U.S. Cl. ..................... 426/332; 426/643; 426/652
[58] Field of Search ............... 426/643, 652, 654, 332

[56] References Cited

FOREIGN PATENT DOCUMENTS 111661 7/1983 Japan .................................. 426/643

OTHER PUBLICATIONS

Boye et al., *J. Food Sci.*, 53(5):1340–1342, 1988.
Lee et al., *J. Food Sci*, 54(5):1116–1124, 1989.

*Primary Examiner*—Arthur L. Corbin
*Attorney, Agent, or Firm*—Sterne, Kessler, Goldstein & Fox

[57] ABSTRACT

A large number of fish species exhibit protease activity and are therefore unacceptable for preparing processed fish products such as surimi. The present invention is directed to a composition containing alpha-2-macroglobulin for inhibiting protease activity contained in the fish material during the preparation of a processed fish product. Thus, the invention provides suitable protease inhibitors to treat a number of fish species which were previously unsuitable for preparing processed fish products such as surimi.

The present invention also relates to a method of preparing a processed fish product comprising contacting the fish material with alpha-2-macroglobulin in an amount sufficient to neutralize or inhibit the protease contained in the fish material.

In addition, the present invention is directed to a fish product prepared using the composition of this invention and to a fish product prepared according to the method of this invention.

6 Claims, 3 Drawing Sheets

METHOD FOR TREATING FISH WITH ALPHA-2-MACROGLOBULIN

FIELD OF THE INVENTION

The present invention relates to the treatment of fish material with alpha-2-macroglobulin during the preparation of a processed fish product.

BACKGROUND OF THE INVENTION

A wide variety of fish products which provide a ready source of processed fish are now available. Surimi is one such product. Surimi is a paste of minced, washed fish muscle. The washing removes water soluble components as well as removing other contaminants. High quality surimi consists of a paste of such muscle. This is dissolved in a dilute solution of sodium chloride which gels on heating. The surimi can be shaped when in a paste form or shaped and extruded after cooking. The surimi paste is usually provided in frozen form. Substances known as cryoprotectants are added to the surimi mix prior to freezing to increase its storage stability. However, a number of species of fish contain heat stable proteases which break down muscle texture during processing, and thus inhibit the gel forming ability of surimi. Since gel formation is a critical processing requirement, species with heat stable proteases are unsuitable raw materials for the production of acceptable quality fish products such as surimi.

A large number of fish species exhibit protease activity which make them unacceptable for preparing processed fish products. Fish species that contain one such enzyme, alkaline protease, include Hoki and Atlantic Croaker. To date, these fish species, which are in plentiful supply in some parts of the world, have been unsuitable for use in the preparation of surimi.

With the growing demand for imitation seafood products made from surimi, new processing technology is essential so that new sources of fish material can be utilized. Based upon the large numbers of species exhibiting proteolytic activity, suitable protease inhibitors would be an indispensable tool in fish processing technology.

SUMMARY OF THE INVENTION

The invention is directed to a composition for treating fish material during the preparation of a processed fish product comprising alpha-2-macroglobulin in amount sufficient to neutralize or inhibit protease contained in the fish material. Thus, the invention provides a suitable protease inhibitor to treat a number of fish species which were previously unsuitable for preparing processed fish products such as surimi.

The present invention also relates to a method of preparing a processed fish product comprising contacting the fish material with alpha-2-macroglobulin in an amount sufficient to neutralize or inhibit the protease contained in the fish material.

In addition, the present invention is directed to a fish product prepared using the composition of this invention and to a fish product prepared according to the method of this invention.

BRIEF DESCRIPTION OF THE DRAWINGS

FIG. 1 is a bar graph which illustrates the effect of an increasing level of protease inhibitor on gel strength as measured by strain. Various temperature/time treatments were analyzed for each protein concentration.

FIG. 2 is a bar graph which demonstrates the effect of increasing levels of protease inhibitor on gel strength as measured by stress (KPa). Various temperature/time treatments were analyzed for each protein concentration.

FIG. 3 is a bar graph which shows the effect of protease inhibition under various temperature/time treatments. Gel strength was measured by strain.

FIG. 4 is a bar graph which demonstrates the effect of protease inhibition under a number of temperature/time treatments. Gel strength was measured by stress.

FIG. 5 is a bar graph demonstrating a comparison of gel strength (stress and strain) of fish material with and without the use of a protease inhibitor.

DETAILED DESCRIPTION OF THE INVENTION

Figure 1:
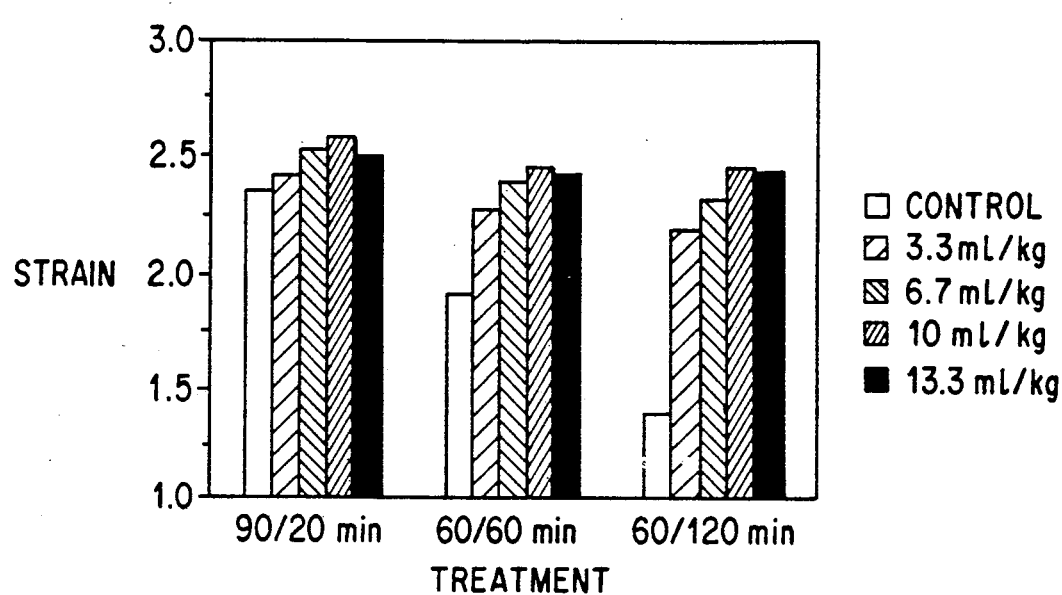
FIGS. 1-5 show the effect of protease inhibition with alpha-2-macroglobulin on surimi gel strength (stress and strain).

The present invention provides a composition for the treatment of fish material during the preparation of a processed fish product comprising alpha-2-macroglobulin in an amount sufficient to neutralize proteases contained in the fish material.

The amount of alpha-2-macroglobulin needed to inactivate the heat stable protease of a particular fish material will vary depending on the amount of protease present in the fish material. The amount of alpha-2-macroglobulin sufficient to neutralize or inhibit the protease present in fish material is an amount necessary to prevent muscle texture breakdown during processing of the fish material. This amount of alpha-2-macroglobulin is typically in the range of 0.1 to 20.0 mls of a 10% (w/v) protein solution (approximately 50% alpha-2-macroglobulin) per kg of fish material. Preferably, the amount of protein solution added is 3.3 to 13.3 mls/kg. Typically, a partially purified alpha-2-macroglobulin is used to treat fish material.

The alpha-2-macroglobulin of the present invention may be obtained from any mammal. Preferably, the alpha-2-macroglobulin is a bovine alpha-2-macroglobulin. Conveniently, the bovine alpha-2-macroglobulin is extracted from bovine plasma. Other mammalian plasma sources for obtaining the alpha-2-macroglobulin of the present invention include but are not limited to ovine, porcine, and equine. Alternatively, the alpha-2-macroglobulin of the present invention may be obtained by recombinant DNA technology well known to those of skill in the art.

The alpha-2-macroglobulin of the present invention may be in lyophilized form to be reconstituted for use by the addition of a suitable diluent, or alternatively, it may be in the form of an aqueous solution.

For reconstitution of a lyophilized product in accordance with the present invention, one may employ a sterile diluent, which may contain materials generally recognized for approximating physiological conditions or conditions suitable to optimize the protease inhibition activity of the alpha-2-macroglobulin of the present invention.

When used as an aqueous solution, the alpha-2-macroglobulin composition of the present invention, for the most part, will contain many of the same substances described above for the reconstitution of a lyophilized product.

In a further aspect, the invention provides a method of preparing a processed fish product comprising treating the fish material with alpha-2-macroglobulin in a manner and in a sufficient amount to neutralize or inhibit the protease contained in the fish material. The alpha-2-macroglobulin needs to be added at a time when it is effective to inhibit the proteases. The effect of the proteases is most noticeable on heating. Thus the inhibitor must be present before heating commences. Desirably it is added prior to freezing. Furthermore, the invention relates to fish products prepared according to the method of the present invention and a fish product prepared using the composition of this invention.

Fish as used in the present invention may be any type of cold-blooded aquatic vertebrate, including, but not limited to the class Osteichthyes, the class Chondrichthyes, the class Agnatha and various unrelated aquatic animals.

The fish material may be derived from the whole fish or parts thereof and may be a mixture of several types, classes or species of fish. Conveniently, the fish may be minced, filleted or otherwise prepared to facilitate contacting the fish material with the alpha-2-macroglobulin. Preferably, the prepared material is soaked in a aqueous solution of alpha-2-macroglobulin for a predetermined time and temperature in order to effect neutralization of the protease before the fish is further processed. Depending upon the temperature of incubation, the time may range from 20 minutes to 20 hours. A typical time will be 20 to 120 minutes with the incubation temperature ranging between 25° to 90° C. The alpha-2-macroglobulin of the present invention may also be added to the processed fish product after processing. The addition of alpha-2-macroglobulin after processing may or may not follow a previous protease neutralization step with alpha-2-macroglobulin.

Using the composition of the present invention, it is possible to prepare completely acceptable fish products from fish material that had previously been considered unsuitable for processing. Criteria for determining acceptability of processed fish products such as surimi are well known to those of skill in the art. In particular, these standards are based on surimi gel strength as analyzed by stress and strain.

A particular advantage of the preferred embodiment of the invention is that the mammalian alpha-2-macroglobulin is an extract from a food product and thus is a much more acceptable additive from the point of view of public health authorities. This is in stark contrast to other artificial additives. Furthermore, the presence of the alpha-2-macroglobulin during storage (after processing) of the prepared fish product may act to prevent residual protease activity from destroying the gel texture. Thus, the alpha-2-macroglobulin of the present invention may be incorporated into the surimi along with the other stabilizers and cryoprotectants, after the washing and dehydration step and before the freezing stage.

A composition of the invention, containing alpha-2-macroglobulin as the active protease inhibitor, may be prepared in crude form from mammalian plasma and then used to neutralize or inhibit the heat stable alkaline protease and other proteases present in some fish tissue. The alpha-2-macroglobulin of the present invention may be obtained from plasma by using well known protein purification techniques.

In general, the plasma is separated from blood by centrifugation. After obtaining the plasma, the alpha-2-macroglobulin may be purified by one or a combination of techniques including salt fractionation, ion-exchange chromatography, molecular-sieve chromatography and affinity chromatography.

The protease inhibitor, bovine alpha-2-macroglobulin, can, for example, be prepared from bovine plasma by a salt fractionation technique. The technique uses different concentrations of ammonium sulphate to precipitate unwanted gamma-globulin fractions, leaving the desired alpha-2-macroglobulin in the supernatant. Finally, a higher concentration of ammonium sulphate may be added to precipitate the active alpha-2-macroglobulin from the supernatant, which is collected and further processed to remove unwanted residual salts. A solution of the prepared alpha-2-macroglobulin may then be used to treat prepared fish material. Alpha-2-macroglobulin obtained by the salt fractionation technique may be further purified by other purification techniques well known to those of skill in art including ion exchange, gel filtration chromatography, dye-ligand affinity chromatography or zinc chelate chromatography. However, the alpha-2-macroglobulin obtained by salt fractionation is suitable for use in the present invention.

Having now generally described the invention, the same will be more readily understood through reference to the following examples which are provided by way of illustration, and are not intended to be limiting of the present invention, unless specified.

EXAMPLE I

Purification of alpha-2-macroglobulin

A crude alpha-2-macroglobulin rich solution was prepared by ammonium sulphate precipitation technique. Bovine serum was diluted with an equal volume of 0.9% (w/v) NaCl in water. Solid ammonium sulphate was then added to the diluted serum to a concentration of 38% (w/v) of the total volume and the solution then stirred for 3 hours. The precipitated contaminating gammaglobulin fraction was then removed by centrifugation and discarded and the alpha-2-macroglobulin rich supernatant collected.

Solid ammonium sulphate was then added to the supernatant to bring the ammonium sulphate concentration to 55% and the mixture stirred for 3 hours. An alpha-2-macroglobulin rich precipitate was collected by centrifugation and the supernatant discarded. The alpha-2-macroglobulin rich precipitate was then extensively dialyzed against 0.9% NaCl to remove the ammonium sulfate. The solution was then concentrated to 10% (w/v) protein and can be used at that concentration.

Alpha-2-macroglobulin obtained by ammonium sulfate precipitation may be further purified by ion exchange, gel filtration chromatography, dye-ligand affinity chromatography or zinc chelate chromatography. However, the alpha-2-macroglobulin purified by the salt precipitation technique (approximately 50% alpha-2-macroglobulin) is suitable for use at a total protein concentration of 1g per kilogram of surimi. The amount of alpha-2-macroglobulin needed to inactivate the heat stable protease of a particular fish material will vary depending on the amount of protease present in the fish meat.

There are a number of other methods that can be used to prepare the protein. These include:

1. Gel filtration using Sephadex G200 (Ganrot, P.O., *Clin Chim Acta* 13:597-601 (1966)).
2. DEAE cellulose (Menhl, J.W., et al., *Soc. Exp. Biol. Med.* 122:203-210 (1966)).
3. Rivanol Precipitation (Steinbuch, M., et al., *Nature* 205:1227-1228 (1965)).
4. Polyethylene Glycol Precipitation (Harpel, P.C., *J. Exp. Med.* 132:329-352 (1970)).

Bovine alpha-2-macroglobulin has a molecular weight of approximately 725,000 Daltons.

To reduce protein denaturation and bacterial growth the process is carried out at 4° C. Bacterial proteases readily inactivate alpha-2-macroglobulin.

The alpha-2-macroglobulin can be stored as a solution at 4° C. or stored as a frozen solution at −18° C. or as a freeze-dried powder and reconstituted before use. The alpha-2-macroglobulin is easily denatured and inactivated, especially by bacterial proteases, and therefore should not be stored for long periods of time in solution.

In surimi production, the alpha-2-macroglobulin can be incorporated into the surimi along with the other stabilizers and cryoprotectants, after the washing and dehydration step and before the freezing stage.

EXAMPLE II

Treatment of fish material with alpha-2-macroglobulin 10 kg blocks of frozen surimi prepared from hoki are thawed partially until they can be cut in suitable cutting apparatus. It is then separated into 1500 g lots and put into a bowl chopper for 15 minutes with salt and water being added to bring about dissolution of the protein in the surimi. The salt is added to achieve a 2% concentration in the final product with water being added to achieve a 78% moisture content. These two additives will be varied dependent upon the moisture content of the initial frozen block. However, each comparative trial takes surimi from the same block.

The alpha-2-macroglobulin produced in Example 1 is added during chopping in the bowl chopper.

The surimi is then incubated at various temperatures for various times as referred to in the attached figure.

Gel strength is usually comprised of a firmness component and an elasticity component. The firmness is indicated by measuring the stress of the product, while the elasticity is measured by the strain. These properties in accordance with this invention were measured on a modified Brookfield viscometer which briefly employs a probe penetrating into the cooked surimi and the probe is subjected to a force to move it sideways through the surimi. People skilled in the art will know the steps necessary to obtain a measure of the stress and strain characteristics of a gel using this apparatus. The modified Brookfield viscometer is essentially a torsion test.

Controls referred to in FIGS. 1 to 5 have no alpha-2-macroglobulin added.

Figure 2:
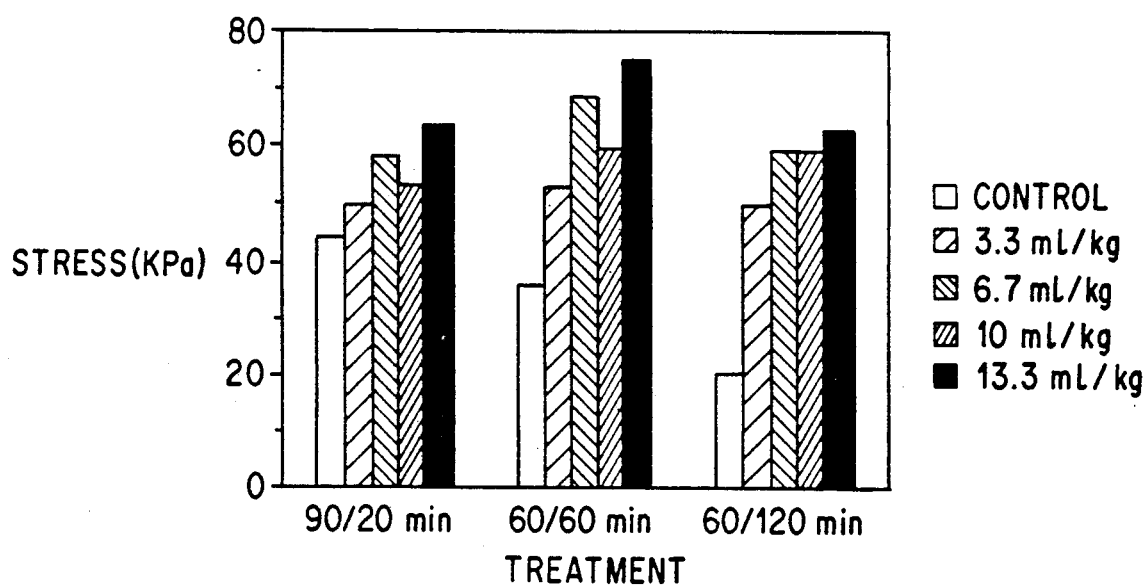

The effect of increasing the level of alpha-2-macroglobulin was tested for inhibition of protease. The results are shown in FIGS. 1 and 2. Three different temperature/time incubation steps were performed to generate each bar graph. Specifically, a 90° C./20 minute incubation, a 60° C./60 minute incubation, and a 60° C./120 minute incubation was performed. In FIG. 1, gel strength was analyzed by torsion shear strain while in FIG. 2, the gel was assessed by torsion shear stress. For each incubation, various amounts of alpha-2-macroglobulin was added per kg of fish material, ranging from 3.3 to 13.3 mls of the 10% (w/v) protein solution containing alpha-2-macroglobulin.

The results demonstrated that by treating the fish material with alpha-2-macroglobulin, even the lowest concentration was sufficient to greatly increase surimi gel strength over the control. Thus, amounts of alpha-2-macroglobulin which were effective to neutralize or inhibit protease activity ranged from 3.3 mls/kg to 13.3 mls/kg. The amount of alpha-2-macroglobulin needed to inactivate the heat stable protease of a particular fish material will vary depending on the amount of protease present in the fish meat. This amount of alpha-2-macroglobulin may easily be predetermined experimentally on various fish species and combinations of fish species. Once determined, alpha-2-macroglobulin may then be used to prepare surimi from a number of species which contain protease activity. Typically, a total protein concentration of 1g of the 10% (w/v) protein solution containing alpha-2-macroglobulin per kilogram of fish material can effectively neutralize protease activity.

The 60° C. incubation (60 and 120 minutes) showed the most drastic increase in gel strength over the control. This may result from the fact that the optimum temperature for alkaline protease activity is near 60° C. whereas the 90° C. incubation may tend to inactivate the protease to some extent. Indeed, alkaline protease isolated from atlantic menhaden (Brevoortia tyrannus) was demonstrated to degrade surimi gels optimally at 60° C. at a pH of 7.5 to 8.0 (Boye et. al., *J. Food Sci.*, 53(5):1340-1342 (1988)). Although the 90° C. treatment may be used to increase gel strength in this case, it may not be effective for all heat stable proteases. Also, the increased costs of excessive temperature treatment over standard thermal processing as well as the potential reduction in nutritional value of the surimi, makes alpha-2-macroglobulin treatment a more attractive alternative. Furthermore, thermal processing of surimi is usually preformed at temperatures of 50°-70° C. and thus according to the results, alpha-2-macroglobulin addition before thermal processing would be effective in making acceptable quality surimi.

Figure 3:
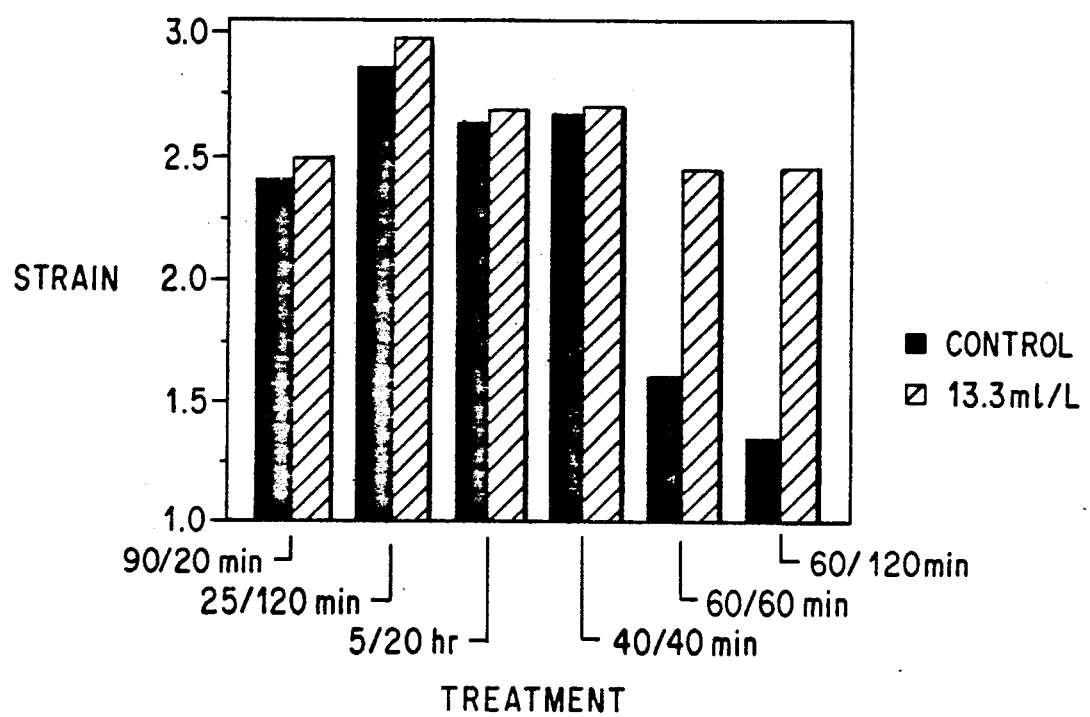
Figure 4:
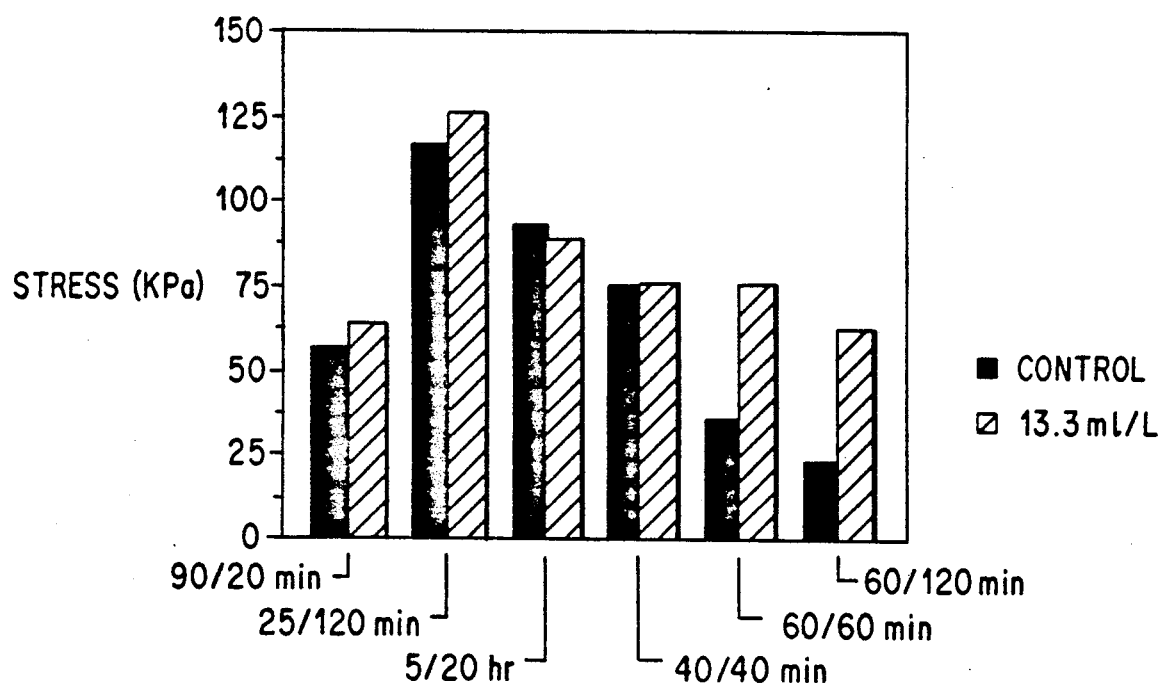

The effect of various heat treatments on protease inhibition was demonstrated in FIG. 3 and 4. Six different temperature/time incubation steps were performed to generate each bar graph. Specifically, 90° C./20 minute, 25° C./120 minute, 5° C./20 hour, 40° C./40 minute, 60° C./60 minute, and 60° C./120 minute incubations were performed. In FIG. 3, gel strength was analyzed by torsion shear strain while in FIG. 4, the gel was assessed by torsion shear stress. For each incubation, 13.3 mls of the alpha-2-macroglobulin solution obtained in example 1 was added per kg of fish material.

As shown in FIGS. 3 and 4, surimi gel strength was increased dramatically after the 60° C./60 min. and 60° C./120 min. incubation period. Thus, the alpha-2-macroglobulin treatment effectively inhibited the protease activity, resulting in completely satisfactory processed fish product.

Figure 5:
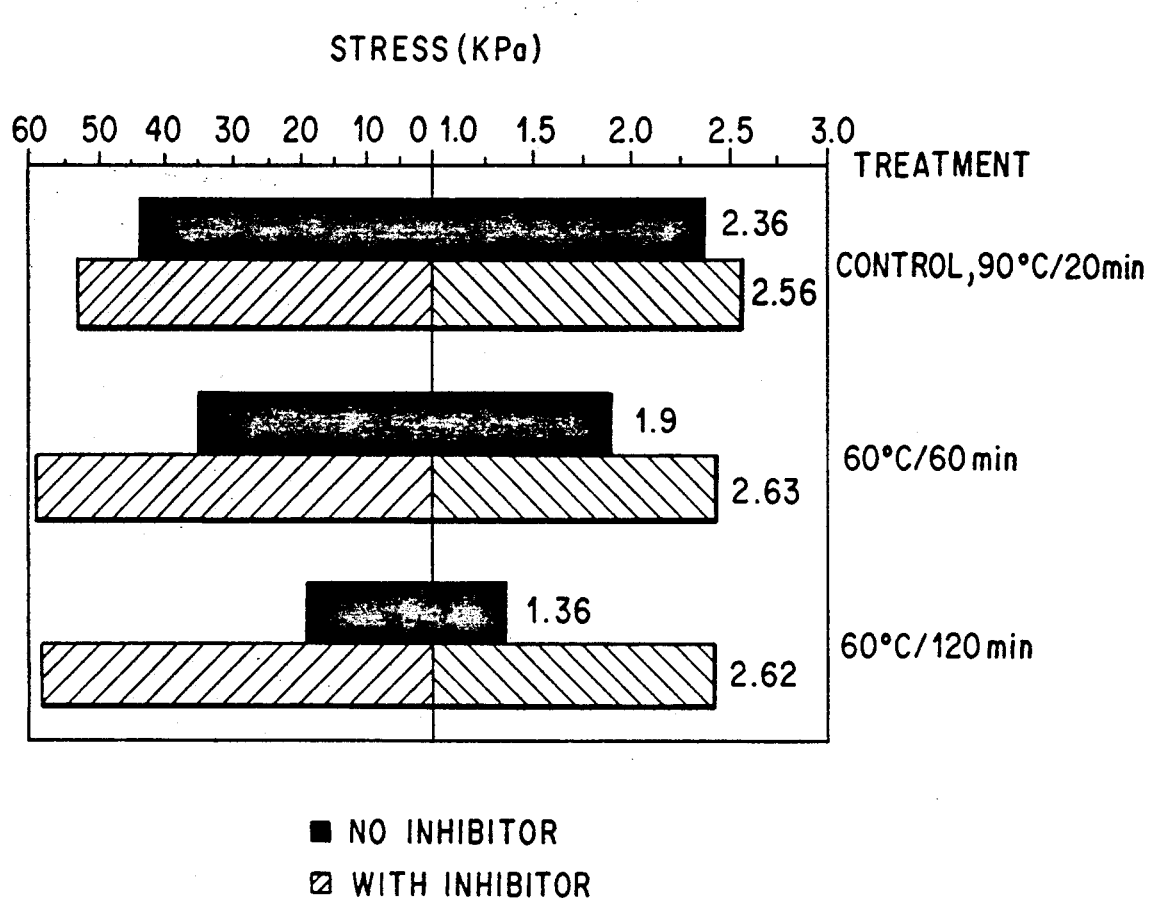

FIG. 5 demonstrates a comparison of surimi gel strength (stress and strain) of Hoki fish material with and without treatment with the alpha-2-macroglobulin protease inhibitor. Three different temperature/time incubation steps were performed to generate the comparison with and without treatment. Specifically, a 90° C./20 minute incubation, a 60° C./60 minute incubation, and a 60° C./120 minute incubation was performed. Gel strength was analyzed by torsion shear strain and by torsion shear stress. For each incubation, 10 mls of the alpha-2-macroglobulin solution obtained in example 1 were added per kg of fish material.

The results in FIG. 5 demonstrate the effectiveness of alpha-2-macroglobulin to dramatically increase surimi gel strength.

These results effectively demonstrate that treatment of fish material with alpha-2-macroglobulin allows production of a completely satisfactory processed fish product from a species which was previously unsuitable for the production of acceptable quality surimi.

What is claimed is:

1. A method of preparing a processed fish product comprising treating fish material with alpha-2-macroglobulin in an amount and in a manner sufficient to neutralize or inhibit protease contained in the fish material.

2. The method of claim 1, wherein said alpha-2-macroglubulin is obtained from a mammal.

3. The method of claim 2, wherein said mammal is selected from the group consisting of bovine, ovine, porcine, and equine.

4. The method of claim 1, wherein said alpha-2-macroglobulin is obtained from mammalian plasma.

5. A fish product prepared according to the method of any one of claims 1-4.

6. The fish product of claim 5, wherein said fish product is surimi.

* * * * *